No. 4,431. REISSUED JUNE 20, 1871.

H. O. LOTHROP.

MACHINE FOR MAKING WIRE FERRULES.

2 SHEETS—SHEET 1.

Witness.
George E. Bond
Edwin H. Nilson

Inventor.
Henry O. Lothrop
By W. H. Clifford
Atty

No. 4,431.

REISSUED JUNE 20, 1871.

H. O. LOTHROP.

MACHINE FOR MAKING WIRE FERRULES.

2 SHEETS—SHEET 2.

Witness.

George E. Bird.

Edwd H. Wilson

Inventor.

Henry O. Lothrop

Per Wm H. Clifford atty

UNITED STATES PATENT OFFICE.

HENRY O. LOTHROP, OF MILFORD, MASSACHUSETTS, ASSIGNOR OF ONE-HALF INTEREST TO ALBERT H. GILMAN.

IMPROVEMENT IN MACHINES FOR MAKING WIRE FERRULES.

Specification forming part of Letters Patent No. 95,918, dated October 19, 1869; reissue No. 4,431, dated June 20, 1871.

*To all whom it may concern:*

Be it known that I, HENRY O. LOTHROP, of Milford, in the county of Worcester and Commonwealth of Massachusetts, have invented a new and useful Manufacture of Wire Tubing for Ferrules, as well as in the Machines for producing the same; and I hereby declare the following to be a full, clear, and exact description thereof, reference being had to the accompanying drawing forming a part of this specification, in which—

Figure 1:
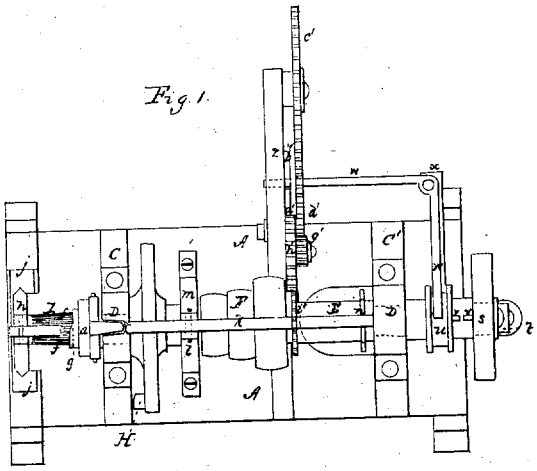
Figure 6:
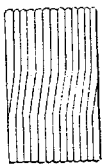
Figure 2:
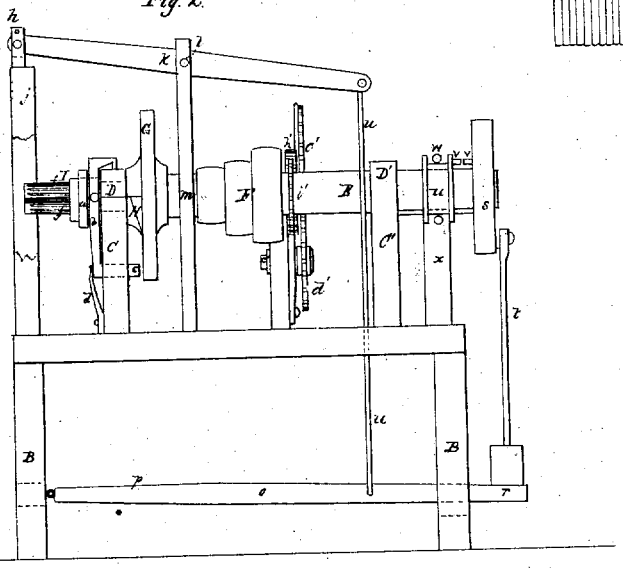
Figure 3:
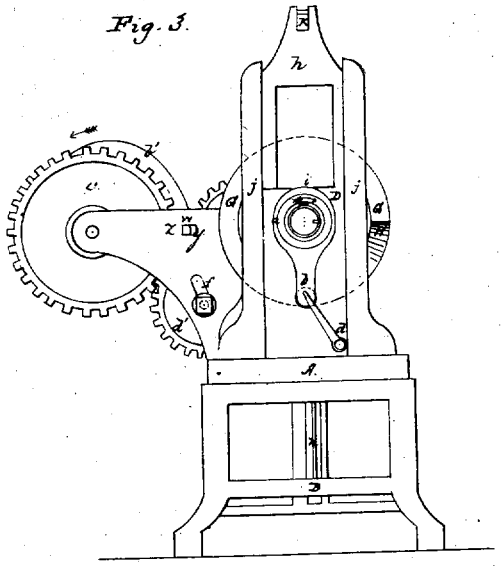
Figure 5:
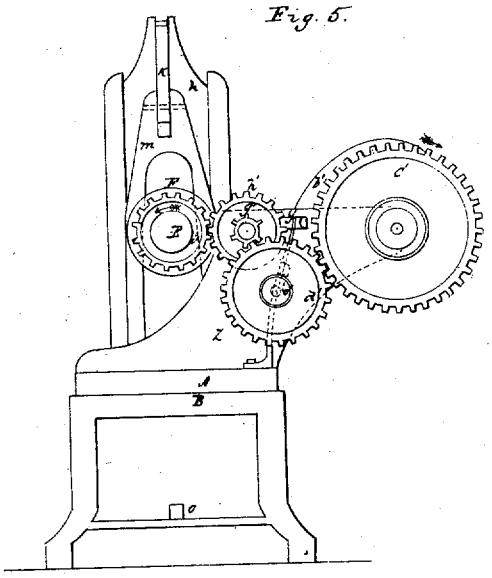
Figure 4:
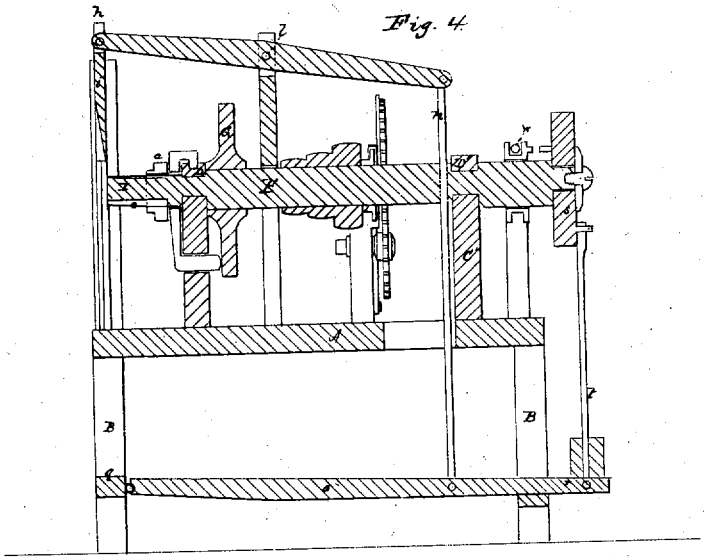

Figure 1 is a plan. Fig. 2 is a side elevation. Fig. 3 is a front-end elevation. Fig. 4 is a vertical central longitudinal section. Fig. 5 is a vertical and transverse section of a machine embodying one portion of my invention. Fig. 6 is a ferrule embodying the latter portion of my invention.

My invention consists, first, in an improved manufacture of coiled-wire tubing for ferrules by forming an offset in each coil, so that each ferrule, when cut from the cylinder, shall present a flush or evenly-finished edge or surface; second, my invention relates to the construction of a machine whereby the cylinder provided with the offset, as described, shall be made up from the wire and the united layers of wire soldered together; also, to a means for cutting from such cylinder a series of ferrules of equal length, the whole being in the manner hereinafter explained.

My machine, as illustrated in this instance, is composed of a rotary arbor supported on suitable bearings, and provided with a driving-pulley, the arbor having a grooved or toothed mandrel, which may be tapering in form, upon which the wire is coiled and the cylinder made up, a beater or burster being loosely disposed about the mandrel, and having intermittent longitudinal movements imparted to it upon such mandrel at short intervals, a sliding cutter being arranged immediately in front of the mandrel, and operated in such manner as to cut, each in regular succession, from the cylinder formed upon such mandrel, as to project beyond the free end of the same a number of sections of ferrules of suitable length to suit the particular purpose for which they are intended.

A shows a table with standards B B. C C′ show the supports of the arbor E, which has the driving-pulley F disposed about midway between the supports C C′, and also the disk G fixed to it immediately in the rear of its support C, the outer face having the wiper-cam H. I shows the grooved or toothed mandrel, tapering in form to accommodate itself to the lessening of the diameter of the cylinder by reason of the reduction of its temperature, it being first applied in a heated state. The taper is to prevent the adhesion of the coil to the mandrel by contraction as the process of winding on the wire progresses. A tubular sleeve, *a*, loosely encompasses a portion of the mandrel immediately forward of the support C, such sleeve being supported about the mandrel, and prevented from revolving with it by means of a shipper, *b*, which surrounds it and is pivoted to its opposite sides, the upper extremity of the shipper being pivoted to the upper part or box of the arbor-support C, while the lower end of such shipper is given a rearward horizontal bend, *c*, which passes through the supports C and impinges against the outer face of the disk G or its wiper H, before mentioned as applied to the disk G, the shipper being maintained in contact with the disk by a spring, *d*, suitably applied to it. Upon the face of the mandrel is the longitudinal axial groove *e*, from end to end of the mandrel, and the periphery of the mandrel has the teeth *f* of about uniform depth till they reach the outer, or nearly the outer, extremity of the mandrel, where they terminate at a short inclination, leaving the periphery near about the end smooth. These teeth are formed in the shape of saw-teeth, receding in a direction reverse to that of the rotation of the mandrel. The end of the mandrel is left smooth to form an even surface for the cutter when employed to cut the cylinder at this point. The revolution of the disk G by means of its wiper H imparts short and quick intermittent movements of the sleeve *a*, which I term the beater, because employed to beat up the coils of wire into a compact body as they accumulate about the mandrel. The forward movement of the beater advances the coils along the mandrel, while its retreat leaves room for the introduction of a fresh portion of wire.

In Fig. 1 it will be seen that the outer end of the beater *a* is formed with a slight offset or projection, *g*, the purpose of which is to form a corresponding offset in each concentric coil of the cylinder, in order that when any one coil is cut by the cutter of the machine at the termination of this offset it shall leave the section thus cut with a uniformly level face, as seen in Fig. 6, which improves the appearance of the ferrule and also in other respects. The wire of which the ferrule is composed is first passed through a receptacle containing a soldering flux; from thence conducted into a vessel of melted solder, the latter being situated immediately contiguous to the mandrel, in order that the solder taken up and conveyed by it shall remain in a hot and liquid state until the wire comes in contact with the last preceding coil about the mandrel, thus producing a solid cylinder. As the cylinder or ferrule contracts in cooling, and its diameter is thus lessened, the edges of the saw-teeth on the mandrel are forced slightly into the inner surface of the cylinder, which, while permitting of a motion longitudinally of the mandrel, prevents any rotation on the same. When the operation of the machine commences the extremity of the wire is bent and inserted within the groove *e* of the mandrel, by which means the wire is caused to adhere and wind about the mandrel until the soldered portions of the wire are brought in contact with the teeth of the mandrel. The wire, as it is wound upon the mandrel, is in a state of tension, and as the cooling takes place at once it contracts so as to hug closely the mandrel, thus affording all the resistance required in order to enable the beater to strike up the offset. The cutter for severing the ferrule from the cylinder consists of a sliding cross-head, *h*, carrying a suitable knife, *i*, sharp upon its lower edge, the cross-head being supported and its vertical movements guided by means of perpendicular guides or ways *j j*, the cutting-edge of the knife, when at its highest position, being above the mandrel and descending to a point below such mandrel. The knife is actuated by a horizontal oscillating lever, K, fulcrumed at or about its center to the upper part of the support *m*, rising from the table A, and surmounting the arbor and face-plate, and between the face-plate and the driving-pulley *f*, the forward end of the lever being pivoted to the cross-head *h*, while its rear extremity is connected by means of a rod, *n*, with a second horizontal lever, *o*, at the lower part of the machine-frame, and from end to end thereof, the forward and longer arm *p* of this lever being pivoted to a cross-bar, *q*, making part of the standard B, while the rear and shorter arm *r* of the lever extends a short distance in rear of the standard B′, as shown in the drawing. The rear extremity of the arbor E is placed above that of the lever *o*, and is provided with a crank-wheel, *s*, which wheel is connected with the shorter arm *r* of the lever *o* by a connecting-rod, *t*, in such manner that a revolution of the wheel *s*, by means hereafter set forth, will cause an elevation of the free end of the lever *o* and of the inner end of the upper lever K, with a corresponding depression of the outer end of such lever and of the knife *i*. The movement of the knife is to be so adjusted as to sever the ferrules when a desired number of the coils has been made. This is effected by regulating the number of revolutions the mandrel shall make to one of the crank-wheel which actuates the knife. With this view I mount the crank-wheel *s* loosely upon the arbor and between the crank-wheel and support C′, and apply a grooved disk or shipping-pulley, *u*, the pulley being loose, but compelled to rotate when desired by a spline-and-groove connection. The shipper-pulley *u* and crank-wheel *s* are provided upon their contiguous faces with clutches *v v*, so that when they approach close to each other they will lock, and thus rotate together, and this revolution of the crank-wheel produces one cutting stroke of the knife and severs a ferrule from the coil on the mandrel.

The shipper *u* is thus operated: A bent horizontal lever, *w*, is pivoted at its bend to the top of the post *x*, rising from the table of the machine, and to one side of the standard or support C′, before mentioned, one end of such shipper extending into the groove of the pulley *u*, while its opposite end extends through a slot or guide, *y*, made in a lateral upright or frame, *z*, erected upon the table of the machine, and at one side of the driving-pulley of the arbor, a spring, *a′*, being applied to such upright and pressing upon the inner side of the shipper, and serving to force it against the cam-grade *b′*, fixed to the periphery of the spur-gear *c′*, suitably applied to the outer extremity of the upright. (See Fig. 5.) The gear *c′* meshes into a second gear, *d′*, the pivot *e′* of which is supported within an oblique slot, *f′*, made in the upright *z*, and below the orifice *y*, before mentioned, the last-mentioned gear in turn meshing into a pinion, *g′*, supported also upon the upright *z*, as represented, the said pinion being affixed to the gear *h′*, which meshes into the gear *i′* fixed to the arbor E of the machine, and in close proximity to its driving-pulley. The adjustability of the gear *d′* is the means by which, by the introduction of gears of different sizes, the movements of the knife relative to the mandrel are regulated. The revolution of the arbor E in the direction of its arrow causes a revolution of the gear *i′* and a reverse motion of the gear *h′*, which, by means of its pinion *g′*, effects a counter revolution of the gear *d′* in a direction similar to the driving-gear *i′*, the said gear *d′*, as will be evident, imparting a rotation to the gear *c′* in the direction of its arrow. The described train of gears may be regulated so as to produce as many coils as desired before the cutting takes place.

When the wiper *b′* has reached the free end of the shipper *w* the operation of the gears upon the crank-wheel may be thus described: The revolution of the driving-gear *i′* from this point forces the wiper *b′* of the gear *c′* in contact with the free end of the shipper *w*, and by moving such shipper from its fulcrum effects a rearward movement of its opposite end, by this means forcing the clutch of the pulley *u* in contact with that of the crank-wheel, and imparting a revolution of the latter according to that of the arbor E, the length of the periphery of the wiper *b'* being such as to maintain the union of the pulley *u* and the wheel *s* until the latter has completed a revolution and dropped the knife for the purpose of cutting a ferrule, when the wiper terminates, and permits the shipper to be returned, by means of its spring *a'*, to its normal position, thus breaking the connection of the pulley and wheel and allowing the latter to revolve independently upon the arbor, the lever *o*, before mentioned, thus being allowed to fall by its own gravity and return the knife to its highest position.

Heretofore wire ferrules have been made by being wound upon a mandrel and then removed therefrom and held in the hands of a workman while being soldered. This adds to the expense of the article, and does not produce one so finished as does my invention. Finishing the ends of the coils at each end of the ferrule was also an item of expense.

The offset, before mentioned as a feature of my invention, economizes much labor, and produces a result which cannot be produced by any means in the old process of manufacturing wire ferrules.

What I claim as my invention, and desire to secure by Letters Patent, is—

1. The process of dipping or passing wire through molten solder, in the manufacture of wire ferrules, in order that the wire shall take up some of the solder, and then winding the said wire on a mandrel so as to coil and solder the same at one operation, as herein set forth.

2. The combination, in machines for making wire ferrules, of a rotating coiling-mandrel, a movable collar or equivalent device, having a projection on its face, substantially as described, and mechanism to impart to the said collar at every revolution of the mandrel a quick percussive movement against the coil, in order that the said projection may thereby create a short lateral bend in each successive coil and at the same time force, to a slight extent, the coil thus made toward and off the mandrel, substantially as set forth.

3. In coiling-mandrels, the combination of the tapering-form grooves *f f* and groove *e*, all arranged and operating as set forth.

4. The combination of the beater *a* with the mandrel I, as herein set forth.

5. The mechanism by which the arbor and knife are operated, at the time and in the manner set forth.

6. The combination of devices, as herein set forth, for making soldered-wire ferrule, as described.

HENRY O. LOTHROP.

Witnesses:
SIMON G. GILMAN,
GEORGE E. BIRD.